United States Patent
Aarts

(10) Patent No.: US 10,269,228 B2
(45) Date of Patent: Apr. 23, 2019

(54) ACOUSTICAL PATIENT MONITORING USING A SOUND CLASSIFIER AND A MICROPHONE

(75) Inventor: Ronald M. Aarts, Geldrop (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1023 days.

(21) Appl. No.: 12/996,034

(22) PCT Filed: May 29, 2009

(86) PCT No.: PCT/IB2009/052287
§ 371 (c)(1),
(2), (4) Date: Dec. 3, 2010

(87) PCT Pub. No.: WO2009/153681
PCT Pub. Date: Dec. 23, 2009

(65) Prior Publication Data
US 2011/0087079 A1    Apr. 14, 2011

Related U.S. Application Data

(60) Provisional application No. 61/073,050, filed on Jun. 17, 2008.

(51) Int. Cl.
*A61B 5/00* (2006.01)
*A61B 7/00* (2006.01)
(Continued)

(52) U.S. Cl.
CPC .......... *G08B 21/0461* (2013.01); *A61B 7/003* (2013.01); *G06F 19/00* (2013.01);
(Continued)

(58) Field of Classification Search
CPC .................................................. G08B 21/043
(Continued)

(56) References Cited

U.S. PATENT DOCUMENTS 5,213,108 A * 5/1993 Bredesen et al. ............. 600/528
5,797,852 A    8/1998 Karakasoglu et al.
(Continued)

FOREIGN PATENT DOCUMENTS

CN         1741128 A      1/2006
DE    102004033907 A1    2/2006
(Continued)

OTHER PUBLICATIONS

Istrate D, et al.; Generic implementation of a distress sound extraction system for elder care; [Conference Proceedings. Annual International Conference of the IEEE Engineering in Medicine and Biology Society (IEEE Cat. No. 06CH37748), 4 pp. IEEE, Piscataway, NJ, USA, 2006, CD-ROM pp. 13 Ref.] (abstract, marked).
(Continued)

*Primary Examiner* — Sean P Dougherty

(57) ABSTRACT

When monitoring a patient, acoustic events (e.g., coughs, snores, impact sounds, verbalizations, etc.) relevant to the patient's status are detected by a microphone array (12) and timestamped. Detected event signals generated by the microphone array (12) are filtered to identify signatures such as zero crossings, corner frequencies, amplitude, pitch, etc., for classification purposes. The filtered signals are digitized and classified into one of a plurality of acoustic event classes (e.g., snore, cough, wheeze, breath, etc.) and/or subclasses. The classified events are displayed to a user (e.g., graphically, textually, etc.) with their timestamps to indicate chronology. A user can review the acoustic events, select one or more events, and listen to a recording of the selected event (s). Additionally, specified acoustic events can trigger an alarm to alert a nurse or the like that the patient requires immediate attention.

17 Claims, 3 Drawing Sheets

(51) Int. Cl.
*G06F 19/00* (2018.01)
*G08B 21/04* (2006.01)

(52) U.S. Cl.
CPC ....... *G06F 19/3418* (2013.01); *G08B 21/043* (2013.01); *A61B 5/4806* (2013.01)

(58) Field of Classification Search
USPC .................................................. 600/529, 586
See application file for complete search history.

(56) References Cited

U.S. PATENT DOCUMENTS

| | | | |
|---|---|---|---|
| 6,063,043 A * | 5/2000 | Meyer et al. ................. | 600/586 |
| 6,201,476 B1 * | 3/2001 | Depeursinge ......... | A61B 5/1117 340/529 |
| 6,261,238 B1 * | 7/2001 | Gavriely ................ | A61B 5/087 600/532 |
| 6,425,874 B1 * | 7/2002 | Sandler .................. | A61B 7/008 600/586 |
| 6,629,937 B2 * | 10/2003 | Watrous ........................ | 600/586 |
| 7,170,404 B2 | 1/2007 | Albert | |
| 7,717,110 B2 * | 5/2010 | Kane et al. ............... | 128/204.21 |
| 7,806,833 B2 * | 10/2010 | Thiagarajan et al. ........ | 600/528 |
| 7,914,468 B2 * | 3/2011 | Shalon et al. ................ | 600/590 |
| 8,352,629 B2 * | 1/2013 | Steadman et al. ............ | 709/232 |
| 2002/0013538 A1 * | 1/2002 | Teller .................... | A61B 5/0002 600/549 |
| 2005/0198588 A1 * | 9/2005 | Lin ..................... | G06F 3/04855 715/784 |
| 2006/0017560 A1 | 1/2006 | Albert | |
| 2006/0064037 A1 * | 3/2006 | Shalon et al. ................. | 600/586 |
| 2006/0212273 A1 * | 9/2006 | Krausman et al. ........... | 702/189 |
| 2006/0256660 A1 * | 11/2006 | Berger ...................... | G01S 5/20 367/124 |
| 2008/0114260 A1 * | 5/2008 | Lange et al. .................. | 600/529 |
| 2008/0114266 A1 * | 5/2008 | Shen ....................... | A61B 7/04 600/586 |
| 2008/0120784 A1 | 5/2008 | Warner | |
| 2008/0243007 A1 * | 10/2008 | Liao et al. .................... | 600/486 |
| 2008/0243016 A1 * | 10/2008 | Liao et al. .................... | 600/532 |
| 2008/0306367 A1 | 12/2008 | Koehler et al. | |
| 2008/0319277 A1 * | 12/2008 | Bradley ...................... | 600/301 |
| 2010/0087746 A1 * | 4/2010 | Radzievsky et al. ......... | 600/528 |
| 2011/0125044 A1 * | 5/2011 | Rhee et al. ................... | 600/534 |

FOREIGN PATENT DOCUMENTS

| | | |
|---|---|---|
| DE | 102005053109 A1 | 5/2007 |
| GB | 2240392 A | 7/1991 |
| JP | 2003038460 A | 2/2003 |
| WO | 00/20047 | 4/2000 |
| WO | 0115602 A1 | 3/2001 |
| WO | 0062664 | 8/2002 |
| WO | 2005074361 A2 | 8/2005 |
| WO | 2006137067 A2 | 12/2006 |

OTHER PUBLICATIONS

Jianfeng,C., et al.; An automaic acoustic bathroom monitoring system; [IEEE International Symposium on Circuits and Systems (ISCAS) (IEEE Cat. No. 05CH37618), 1750-1753 vol. 2 IEEE, Piscataway, NJ, USA, 2005, 6 vol. (cclxxxix +6335) pp. 4 Ref.] (abstract, marked).

* cited by examiner

ACOUSTICAL PATIENT MONITORING USING A SOUND CLASSIFIER AND A MICROPHONE

CROSS REFERENCE TO RELATED APPLICATIONS

This application claims the benefit of U.S. provisional application Ser. No. 61/073,050 filed Jun. 17, 2008, which is incorporated herein by reference.

The present innovation finds particular application in patient monitoring systems. However, it will be appreciated that the described technique may also find application in other monitoring systems, other patient treatment scenarios, other data collection techniques, and the like.

Many patients are monitored to sense vital signs and display related information. In critical care units of hospitals, such monitoring allows continuous supervision of a patient without continuous attendance, thus improving patient care. Remote monitoring systems permit some patients that in years past would have been kept at the hospital, to move to assisted living or home care environments. Monitor displays resemble computer monitors and use superficially similar technology. Sensing elements of the monitor typically contact the patient physically to measure pulse rate, $SpO_2$, blood pressure, and the like. Additionally, some monitors, such as electrocardiogram (ECG) and electroencephalogram (EEG) monitors have electrical contact with the patient.

In some cases however, the patient needs not immediate care, but rather monitoring of signs that may indicate that care is necessary later on, or that may predict serious events. Such signs may differ from the signals obtained by electrophysical monitors, e.g. coughing, snoring, screaming, and impact sounds, the latter two of which can be common during epilepsy seizures. Impact sounds may occur if someone hits the furniture around the bed, the bed itself (e.g., during a seizure), the floor (e.g., if the patient falls out of the bed or falls on the way from a bathroom), etc.

Current patient monitoring measures usually only electrophysical signals and therefore may miss signs indicating that the patent needs care, such as coughing, snoring, screaming, and impact sounds. Systems that measure electrophysical signals in a reliable way are usually obtrusive, not well suited for extended periods of use, and hence uncomfortable or otherwise patient unfriendly.

The present application provides new and improved systems and methods for monitoring patients and collecting audible patient status information, which overcome the above-referenced problems and others.

In accordance with one aspect, a patient monitoring system includes one or more microphones that detect acoustic events generated by a patient and generate signals comprising information describing the acoustic events, a processor that timestamps the acoustic event signals, and a classifier that classifies each acoustic event signal into one of a plurality of acoustic event classes.

In accordance with another aspect, a method of monitoring a patient includes detecting an acoustic event generated by the patient, timestamping an acoustic event signal that includes information related to the acoustic event, classifying the acoustic event into one of a plurality of acoustic event classes as a function of the identified signatures, and storing a classified acoustic event with the timestamp.

According to another aspect, an apparatus for monitoring a patient includes means for detecting an acoustic event generated by the patient, means for timestamping an acoustic event signal that includes information related to the acoustic event, and means for filtering the acoustic event signal to identify signatures associated with the acoustic event signal. The apparatus further includes means for digitizing the acoustic event signal, and means for classifying the acoustic event into one of a plurality of acoustic event classes as a function of the identified signatures. Additionally, the apparatus includes means for storing a classified acoustic event with the timestamp, and means for displaying the classified acoustic events with respective timestamps for review and playback.

One advantage is that additional medically-relevant information is collected.

Another advantage resides in storing acoustic event information for later review.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
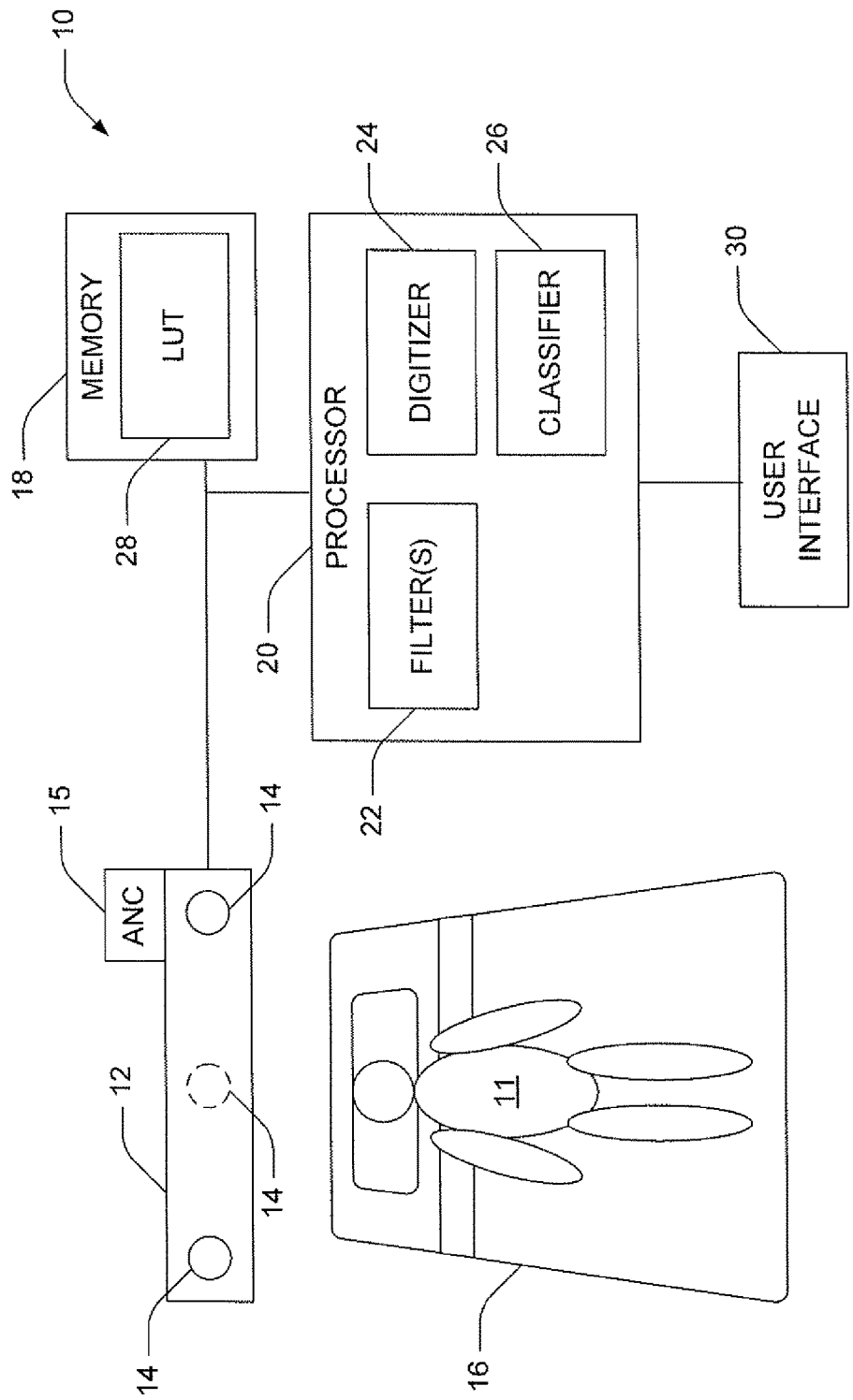
FIG. 1 illustrates a patient monitoring system (PMS) that detects acoustic events in the vicinity of a patient for real-time or delayed review by a healthcare provider (e.g., a nurse, physician, etc.).

FIG. 1 illustrates a patient monitoring system (PMS) 10 that detects acoustic events in the vicinity of a patient 11 for real-time or delayed review by a healthcare provider (e.g., a nurse, physician, etc.). The system detects, in an unobtrusive and patient-friendly manner, sounds generated by the patient via an adaptive microphone array 12 comprising one or more microphones 14. In one embodiment, the microphone array 12 is a strip (e.g., linear) array having at least two microphones that facilitate triangulating the location source of each acoustic event. For example the strip array may be between 20 cm and 40 cm in length. In another embodiment, the microphone array comprises N microphones, where N is an integer greater than 2. In another embodiment, a single microphone is employed.

The microphone(s) 14, adaptive (or directional) microphone array 12, or the like are oriented toward the area of the patient. Extraneous sounds such as noises outside the patient's room, other patients' noises, street traffic, etc., are suppressed. In one embodiment, the array includes an active noise cancellation (ANC) component 15, that employs an ANC technique to cancel unwanted noise (e.g., non-patient-generated acoustic events such as ambient noise in or near the patient monitoring area, a television or radio on in the monitoring area, etc.). The adaptive microphone array is constructed using known techniques, such as those used for speech communication. The microphone array can be positioned anywhere in a patient's room to detect acoustic events generated by the patient. For instance, the array can be mounted or positioned over a patient bed 16 on which the patient rests or sleeps. Alternatively, the array can be ceiling-mounted, recessed in a wall or ceiling, mounted to the patient's bed, carried by the patient, etc. In another embodiment in which the patient's environment includes a plurality of rooms, a plurality of arrays can be provided.

Acoustic events such as coughing, snoring, screaming, impact sounds, etc. are detected by the microphones, and can be logged for later review or monitored in real time by a caregiver. The monitoring system can be used to monitor patients in hospitals, as well as for home use. In one embodiment, the monitoring system provides insight into a patient's sleeping behavior, to learn for instance whether the patient snores, how deeply or often the patient snores, etc. (e.g., to diagnose a sleep disorder such as sleep apnea or the like). Other applications include monitoring young children, the elderly, etc.

A signal relating to an acoustic event detected by the microphone array 12 is stored to a memory 18, and received and analyzed by a processor 20. The processor includes one or more filters 22 through which the acoustic event signal is passed to detect event signatures. Filtered signals are then digitized by a digitizer 24, which may be an analog-to-digital (A/D) converter or the like. One or more classifiers 26 then classify the filtered, digitized signals to identify an acoustic event (e.g., a cough, groan, sneeze, snore, etc.) consistent with the signal. Additionally, a classifier can include subclasses of acoustic events into which a classified acoustic event may be further classified. For instance, events classified as a cough can be further classified as, e.g., a wheezing cough, a productive cough, a gargled cough, a dry cough, etc.

In one embodiment, the filters 22 are bandpass filters, and the processor analyzes event signatures such as zero-crossings, corner frequencies, and the like to identify signal patterns consistent with different acoustic events (e.g., snoring, yawning, coughing, yelling, impact sounds, etc.). The digitized signal information is then operated on by the classifiers, which access a lookup table 28 in the memory 18 to bin detected acoustic events into groups consistent with their respective acoustic signatures. The classification is performed in a manner analogous to music classification and other sounds using a bank of bandpass filters, circuits for measuring average zero crossing time, pitch monitors, energy or amplitude monitors, and the like. The classifier may be pre-trained to recognize various medically significant sounds and to discard normal background noise. The classifier may be fine-tuned with an additional teaching session to adapt it specifically to each patient. For example, the classifier(s) can be made by modifying a music classifier in such a way that the desired classes of acoustic events are generated. That is, a music classifier that classifies songs into different classes or genres as a function of features or signatures of a recording of the song can be modified to analyze different features consistent with the described acoustic events to classify detected acoustic events into various acoustic event classes.

In another embodiment, the classifier is trained for each patient individually. For instance, a nurse or other healthcare technician can monitor the patient, and upon the occurrence of an acoustic event, can identify the acoustic event as belonging to a specific event class, including but not limited to cough, snore, breath, gargled breath, yell or scream, verbal speech, groan, thump, belch, flatulence, and the like. Once the classifier is trained, the patient can be monitored in the absence of the technician.

In another embodiment, the patient is monitored for a predetermined period (e.g., a night), and a technician later reviews the recording and identifies different sounds as belonging to respective classes of acoustic events.

In yet another embodiment, a universal classifier is trained with a range of acoustic event sounds and is employed for patients without individual patient-specific training. On one variation, the universal classifier can be trained to customize it to a specific patient.

Additionally, the processor 20 timestamps the signals as they are detected, and outputs a chronologically or otherwise organized display of detected acoustic events on a user interface 30. For example, sounds can be grouped by class for display or a count, or count per unit time, of each type of noise can be displayed, or the like. Identified sounds can be sent to a central monitoring station, can be stored in text, can be stored in medical hospital databases, or the like. A healthcare provider then reviews the output for treatment, diagnosis, therapy planning, or the like. In one embodiment, an identifier of the sound is displayed textually, and the healthcare provider is given the option of listening to the sound.

Sounds that are deemed medically urgent for a patient can trigger an alert of the occurrence to alert a caregiver, medical professional, parent, or the like. For instance, a scream or yell (or series thereof) can be designated as an alarm event that triggers the alarm. Additionally or alternatively, an impact sound followed by an absence of acoustic events of a predetermined duration can trigger an alarm to alert a nurse that the patient may have fallen out of bed an been injured. According to another example, the detection of one or more impact sounds may indicate that the patient is having a seizure, and can trigger the alarm.

In another embodiment, additional inputs to the classifier may be used, such as signals obtained from accelerometers connected to the bed or patient, pressure mats around the bed, signals from other patient parameter or vital signs monitoring devices, cameras, etc., in order to make the classifier more powerful. For instance, information generated by accelerometers can be used to corroborate an acoustic event, to verify that the acoustic event was in fact generated by the patient, etc.

It will be appreciated that the memory 18 stores, and the processor 20 executes, machine-executable instructions for performing any and all of the various functions described herein.

Figure 2:
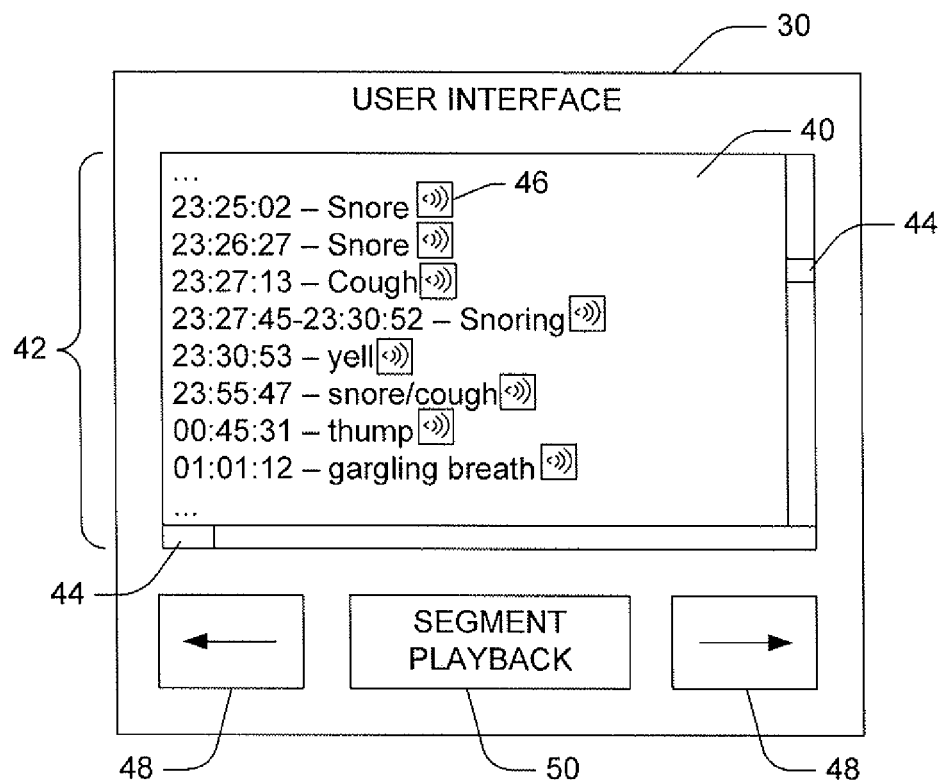
FIG. 2 illustrates the user interface, by which acoustic event information is presented to a user for review.

FIG. 2 illustrates the user interface 30, by which acoustic event information is presented to a user for review. The user interface 30 includes a display 40 on which a plurality of acoustic events 42 are textually described and presented to a user after time stamping and classification. In one embodiment, slider bars 44 are provided, by which the user scrolls vertically and optionally horizontally to view the list of acoustic events. The user can click on, or otherwise select, a selectable icon 46 next to each acoustic event to hear the filtered and digitized version of the acoustic event.

Additionally or alternatively, navigation arrows 48 are provided on the user interface, with which the user navigates through the chronologically ordered acoustic events. The user then selects, clicks on, depresses, etc., a segment playback button or icon 50 to hear the acoustic event.

According to an example, a displayed segment the chronological list of acoustic events 42 includes individual timestamped events. For instance, events classified as "snores" and "coughs" are illustrated, as well as a "yell," a "thump," a "gargled breath" event, etc. In one embodiment, similar and contiguous acoustic events are grouped together to improve presentation to the user. For example, if the system detects acoustic events that are classified as snores during the period from 23:27:45 to 23:30:52, and no other types of acoustic events are classified in that time period, then the Acoustic events are grouped into a set and displayed as a period of snoring spanning the time period for the contiguous events. The user can select the icon 46 for the group of acoustic events and listen to the entire period, or can select the textual description of the group of acoustic events to view individual events in the group and optionally listen to the individual events.

In another embodiment, ambiguity in acoustic event classification can be resolved by the user. For instance, an acoustic event is illustrated as having occurred at 23:55:47, and has been classified as both a snore and a cough. The user can select the playback icon 46 or the segment playback icon 50 to review the sound associated with the event, and can then indicate (e.g., by selecting "snore" or "cough" on the display 40) which acoustic event the user believes to be correct. In another embodiment, ambiguity resolution is resolved automatically by the processor.

Additionally or alternatively, classified acoustic events can be grouped according to class and output on the display for review. For instance, all cough events can be presented together, and a user can click on individual events, or icons 46 or 50, to review the actual recording of a given cough. Individual events can be timestamped to permit the reviewer to determine chronologic relationships therebetween.

Figure 3:
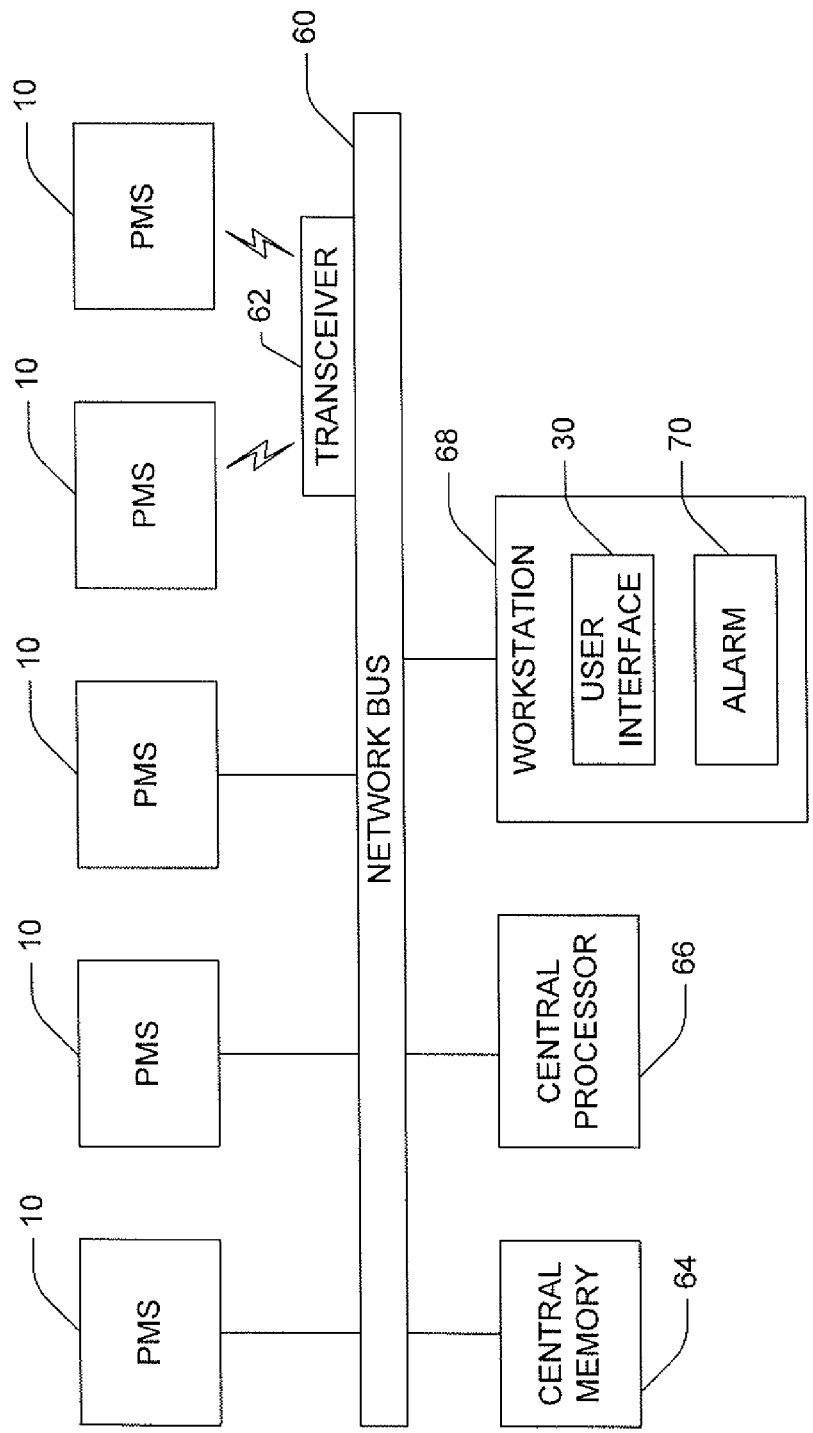
FIG. 3 illustrates a hospital environment in which the system is employed, in accordance with one or more aspects.

FIG. 3 illustrates a hospital environment in which one or more PMS 10 is employed, in accordance with one or more aspects. A plurality of patient monitoring systems 10 are coupled to a network bus 60. Connections between the PMSs and the bus may be wired or wireless. For instance, one or more PMSs can include a transmitter (not shown) that communicates acoustic event information to a transceiver 62 coupled to the bus. For instance, wireless PMSs can communicate with the transceiver using Bluetooth, Zigbee, WiFi, infrared (IR), radio frequency (RF), or any other suitable wireless communication protocol.

Acoustic event information from each of the PMSs is stored to a central memory 64. A central processor 66 accesses the central memory to retrieve acoustic event information for a given patient or PMS in response to a request by a user at a workstation 68. The workstation includes a user interface 30, which may be similar or identical to the user interface of the preceding figures. In one embodiment, detected acoustic events are filtered, digitized, classified, timestamped, grouped, etc., at each respective PMS 10, and each patient's acoustic event record is then stored to the central memory 64, in addition to the memory resident in each respective PMS.

In another embodiment, one or more of the filtering, digitizing, classifying, time-stamping, grouping, etc., steps is performed by the central processor 66. For instance, the central processor can include any and all circuitry (e.g., filters, digitizers, classifiers, etc.) needed to carry out the functions of the PMS 10. In this embodiment, only the microphone array (e.g., with a transmitter) need be located in the patient's room, and signals representing detected acoustic events are transmitted to the central memory and processor for processing.

In another embodiment, the PMS 10 and/or the central processor 66 detects an alert condition, such as a series of acoustic events indicative of an emergency condition. For instance, sequentially detected acoustic events consistent with a yell and a thump can indicate that a patient has fallen out of bed and can trigger an alarm 70 at the workstation to alert a nurse of other healthcare provider that the patient being monitored by the detecting PMS needs immediate attention. The acoustic events triggering the alarm are also logged (e.g., locally at the PMS and/or centrally at the central memory) for later review.

In another embodiment, each patient's acoustic event files are stored in the central memory, e.g., in a hospital database, for future reference when treating or diagnosing the patient.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A patient monitoring system, including:
   one or more microphones configured to detect acoustic events generated by a patient, and generate signals comprising information describing the acoustic events;
   a processor configured to timestamp the acoustic event signals with a timestamp;
   a classifier configured to classify each acoustic event signal into one of a plurality of acoustic event classes;
   a memory configured to store computer-executable instructions, which when executed by the processor, cause the processor to:
   filter the acoustic event signal and identifying signatures associated with the acoustic event signal prior to digitizing the acoustic event signal;
   digitize the acoustic event signal;
   as a function of the identified signatures, classify the acoustic event signal into:
   one of a plurality of acoustic event classes; and
   one of a plurality of subclasses of the one of the plurality of acoustic event classes; and
   trigger an alarm that the patient may have fallen out of a bed by:
   (i) determining an impact sound; and
   (ii) determining that there has been an absence of an acoustic event for a predetermined duration following the impact sound; and
   a user interface configured to display:
   (i) the timestamp and a textual description of one or more classified acoustic events on a display; and
   (ii) a playback icon for selecting and playing a recorded audio file of the acoustic event.

2. The system according to claim 1, wherein:
   the plurality of acoustic event classes includes a cough class; and
   the cough class includes subclasses of at least one of:
   a wheezing cough subclass;
   a productive cough subclass;
   a gargled cough subclass; and
   a dry cough subclass.

3. The system according to claim 1, wherein:
   the plurality of acoustic event classes includes a cough class; and
   the cough class includes subclasses of all of:
   a wheezing cough subclass;
   a productive cough subclass;
   a gargled cough subclass; and
   a dry cough subclass.

4. The system according to claim 1, further including:
   an active noise cancellation component configured to suppress non-patient-generated acoustic event sounds.

5. The system according to claim 1, wherein the acoustic event classes include classes for patient-generated sounds including at least one of a yell, groan, impact sound, belch, or verbal speech.

6. The system according to claim 1, further including one or more filters that detects acoustic event signatures associated with the acoustic event signals, the one or more filters includes a bandpass filter;
   wherein the acoustic event signatures include all of:
   average zero crossing time, amplitude, frequency, one or more corner frequencies, and pitch of the acoustic event signals.

7. The system according to claim 1, wherein the acoustic event classes include classes for patient-generated sounds including all of a yell, groan, impact sound, and belch.

8. A method of monitoring a patient, including:
   detecting, with one or more microphones, an acoustic event generated by the patient;
   timestamping, with a timestamp, an acoustic event signal that includes information related to the acoustic event;
   filtering the acoustic event signal to identify signatures associated with the acoustic event signal prior to digitizing the acoustic event signal;
   digitizing the acoustic event signal;
   as a function of the identified signatures, classifying the acoustic event signal into:
      one of a plurality of acoustic event classes; and
      one of a plurality of subclasses of the one of the plurality of acoustic event classes;
   storing each classified acoustic event with the timestamp; and
   triggering an alarm that the patient may have fallen out of a bed by:
      (i) determining an impact sound; and
      (ii) determining that there has been an absence of an acoustic event for a predetermined duration following the impact sound.

9. The method according to claim 8,
   the plurality of acoustic event classes includes a cough class; and
   the cough class includes subclasses of at least one of:
      a wheezing cough subclass;
      a productive cough subclass;
      a gargled cough subclass; and
      a dry cough subclass.

10. The method according to claim 8, further including:
    using active noise cancellation to suppress ambient sounds when detecting the acoustic event.

11. A patient monitoring system comprising a non-transitory computer-readable medium including computer readable instructions, which when executed by a processor, cause the processor to:
    detect an acoustic event generated by a patient;
    using information from an accelerometer, verify that the acoustic event was generated by the patient;
    timestamp an acoustic event signal that includes information related to the acoustic event;
    filter the acoustic event signal to identify signatures associated with the acoustic event signal prior to digitizing the acoustic event signal;
    digitize the acoustic event signal;
    classify the acoustic event into one of a plurality of acoustic event classes as a function of the identified signatures;
    store a classified acoustic event with the timestamp;
    group acoustic events together into a group, wherein each event within the group:
       has a same class as other events of the group; and
       is contiguous with another event of the group; and
    control a display to display the group to a user.

12. The patient monitoring system of claim 11, wherein the computer readable instructions, which when executed by a processor, further cause the processor to:
    control a display to display an icon corresponding to the group, the icon allowing the user to listen to an entire period of the group.

13. The patient monitoring system of claim 11, wherein the computer readable instructions, which when executed by a processor, further cause the processor to:
    control a display to allow the user to select a textual description of the group to view individual events of the group.

14. The patient monitoring system of claim 11, wherein the computer readable instructions, which when executed by a processor, further cause the processor to:
    train the processor to classify acoustic events for the patient by, upon an occurrence of a specific acoustic event, receiving an input from a user that identifies the specific acoustic event as belonging to a specific event class.

15. The patient monitoring system of claim 11, wherein the computer readable instructions, which when executed by a processor, further cause the processor to:
    control the display the allow the user to scroll vertically and horizontally to view a list of acoustic events.

16. A method of monitoring a patient, including:
    detecting, with one or more microphones, an acoustic event generated by a patient;
    using information from an accelerometer, verifying that the acoustic event was generated by the patient;
    timestamping an acoustic event signal that includes information related to the acoustic event;
    filtering the acoustic event signal to identify signatures associated with the acoustic event signal prior to digitizing the acoustic event signal;
    digitizing the acoustic event signal;
    classifying the acoustic event into one of a plurality of acoustic event classes as a function of the identified signatures;
    storing a classified acoustic event with the timestamp;
    grouping acoustic events together into a group, wherein each event within the group:
       has a same class as other events of the group; and
       is contiguous with another event of the group; and
    controlling a display to display the group to a user by displaying an icon corresponding to the group, the icon allowing the user to listen to an entire period of the group;
    wherein the acoustic event classes include classes for patient-generated sounds including all of a yell, groan, impact sound, and belch.

17. The patient monitoring method of claim 16, further comprising:
    controlling a display to allow the user to select a textual description of the group to view individual events of the group.

* * * * *